US00PP08172P

United States Patent [19]

VandenBerg

[11] Patent Number: Plant 8,172

[45] Date of Patent: Mar. 9, 1993

[54] CHRYSANTHEMUM PLANT NAMED CANTATA

[75] Inventor: Cornelis P. VandenBerg, Salinas, Calif.

[73] Assignee: Yoder Brothers, Inc., Barberton, Ohio

[21] Appl. No.: 745,701

[22] Filed: Aug. 16, 1991

[51] Int. Cl.[5] ..... A01H 5/00

[52] U.S. Cl. ..... Plt./82.4

[58] Field of Search ..... Plt./74.1, 82.4

*Primary Examiner*—Howard J. Locker

*Attorney, Agent, or Firm*—Foley & Lardner

[57] ABSTRACT

A Chrysanthemum plant named Cantata particularly characterized by its flat capitulum form; daisy capitulum type; light pink ray floret color in the red group; diameter across face of capitulum of 76 to 89 mm when fully opened, when grown as a single stem spray cut mum; flowering response in Salinas under normal temperatures is 48 to 52 days after start of short days; flowering response in Bogota, Colombia under temperatures of minimum 6.3 degrees Celsius night and maximum 29 degrees Celsius day is 59 to 63 days; plant height is 84 to 91 cm when grown in Salinas with 6 to 7 long days prior to start or short days; height is 94 to 107 cm when grown in Bogota with 14 long days prior to start of short days; peduncle length of the first lateral at flowering after removing the apical bud without growth regulator applications is 10 to 15 cm when grown in Salinas, and 13 to 20 cm when grown in Bogota; peduncle length of the fourth lateral at flowering is 15 to 25 cm when grown in Salinas, and 18 to 23 cm when grown in Bogota; and excellent tolerance to low night temperatures for bud initiation and flower development.

3 Drawing Sheets

The present invention comprises a new and distinct cultivar of Chrysanthemum, botanically known as *Dendranthema grandiflora,* and referred to by the cultivar name Cantata.

Cantata, identified as 2548 (87-512007), was originated from a cross made by Cornelis P. VandenBerg in a controlled breeding program in Salinas, Calif., in 1986.

The female parent of Cantata was the cultivar identified as Oreo, disclosed in U.S. Plant Pat. No. 6,882, and described as a flat daisy cut spray mum with a purple ray floret color; a diameter of capitulum of 70 to 73 mm; a flowering response in Salinas, Calif. of 47 to 58 days; and in Bogota, Colombia of 58 to 63 days; a plant height in Salinas, Calif. of 91 to 102 cm when grown with 14 long days prior to start of short days; and of 94 to 112 cm when grown in Bogota, Colombia when grown with 17 to 21 long days prior to start of short days; a peduncle length of the first and the fourth lateral of 10 to 15 cm and 13 to 20 cm when grown in Bogota; a terminal spray formation; and an excellent tolerance to low night temperatures for bud initiation and flower development.

The male parent of Cantata was an unnamed seedling, identified as 1033 (83-715009), and described as a white daisy spray cut mum; flowering response to short days of 55 to 64 days in Salinas, Calif., and of 80 days in Bogota, Colombia; a plant height of 69 to 89 cm with 7 to 14 long days prior to start of short days; and a peduncle length of 10 to 13 cm of the first lateral and 15 to 18 cm of the fourth lateral, height and peduncle length both measured in Salinas. The male parent was tested only twice in Colombia and was discarded from the Colombian program in November 1985, because of very slow flowering response, and was discarded completely from all programs in September 1987.

Cantata was discovered and selected as one flowering plant within the progeny of the stated cross by Cornelis P. VandenBerg in January 1988, in a controlled environment in Salinas, Calif.

The first act of asexual reproduction of Cantata was accomplished when vegetative cuttings were taken from the initial selection in March 1988 in a controlled environment in Salinas, Calif., by technicians working under supervision of Cornelis P. VandenBerg.

Horticultural examination of controlled flowerings of successive plantings has shown that the unique combination of characteristics as herein disclosed for Cantata are firmly fixed and are retained through successive generations of asexual reproduction.

Cantata has not been observed under all possible environmental conditions. The phenotype may vary somewhat with variations in environment such as temperature, light intensity and daylength, without, however, any variance in the genotype.

The following observations, measurements and comparisons describe plants grown in Salinas, Calif., and in Bogota, Colombia, under greenhouse conditions which approximate those generally used in commercial greenhouse practice. The low temperature tolerance was determined in repeated flowerings in Bogota, Colombia, with an average minimum low night temperature inside the greenhouse during our trials ranging from 6.3 to 10.0 degrees Celsius.

The following traits have been repeatedly observed and are determined to be basic characteristics of Cantata, which, in combination, distinguish this Chrysanthemum as a new and distinct cultivar:

1. Flat capitulum form.
2. Daisy capitulum type.
3. Light pink ray floret color in the red group.
4. Diameter across face of capitulum of 76 to 89 mm when fully opened, when grown as a single stem spray cut mum.
5. Flowering response in Salinas under normal temperatures is 48 to 52 days after start of short days. Flowering response in Bogota, Colombia under temperatures of minimum 6.3 degrees Celsius night and maximum 29 degrees Celsius day is 59 to 63 days.

6. Plant height is 84 to 91 cm when grown in Salinas with 6 to 7 long days prior to start of short days; height is 94 to 107 cm when grown in Bogota with 14 long days prior to start of short days.

7. Peduncle length of the first lateral at flowering after removing the apical bud and without growth regulator applications is 10 to 15 cm when grown in Salinas and 13 to 20 cm when grown in Bogota. Peduncle length of the fourth lateral at flowering is 15 to 25 cm when grown in Salinas, and 18 to 23 cm when grown in Bogota.

8. Excellent tolerance to low night temperatures for bud initiation and flower development.

The accompanying photographic drawings show typical inflorescence and leaf characteristics of Cantata, with the colors being as nearly true as possible with illustrations of this type.

Sheet 1 is a color photograph of Cantata grown as a single stem spray cut mum.

Sheet 2 is a black and white photograph of three views of the inflorescence of Cantata.

Sheet 3 is a black and white photograph showing the upper and under sides of the leaves of Cantata at 3 stages of development (mature, intermediate and immature). In sheet 2 a measuring tape in centimeters has been added.

Of the commercial cultivars known to the inventor, the most similar in comparison to Cantata is the cultivar Volare, disclosed in U.S. Plant patent application, Ser. No. 07/651,001. Reference is made to attached Chart A, which compares certain characteristics of Cantata to the same characteristics of Volare.

Similar trains are capitulum form and type, flowering response in Salinas, and excellent low night temperature tolerance. Peduncle length of both varieties are comparable. In addition, Cantata and Volare have the same parents. When compared with Volare, Cantata has a much lighter ray floret color, a wider range of diameter of capitulum, and a significant earlier flowering response in Bogota. Cantata also has more vigor than Volare, with Cantata being grown with 6 to 7 long days in Salinas and with 14 long days in Bogota to acquire desired plant height, while Volare is grown with 14 long days in Salinas and with 17 to 21 long days in Bogota to acquire desired plant height for commercial practices.

In the following description color references are made to The Royal Horticultural Society Colour Chart. The color values were determined on plant material grown as a single stem spray mum in Salinas, Calif. on Sep. 12, 1990.

Classification:

*Botanical.*—*Dendranthema grandiflora* cv. Cantata.
*Commercial.*—Daisy spray cut mum.

INFLORESCENCE

A. Capitulum:
*Form.*—Flat.
*Type.*—Daisy.
*Diameter across face.*—76 to 89 mm when fully opened.

B. Corolla of ray florets:
*Color (general tonality from a distance of three meters).*—Light pink (red group).
*Color (upper surface).*—56D.
*Color (under surface).*—56D.
*Shape.*—Straight, oblong, slightly ribbed.

C. Corolla of disc florets:
*Color (mature).*—14B.
*Color (immature).*—144B.

D. Reproductive organs:
*Androecium.*—Present on disc florets only; moderate pollen.
*Gynoecium.*—Present on both ray and disc florets.

PLANT

A. General appearance:
*Height.*—84 to 91 cm when grown in Salinas with 6 to 7 long days prior to start of short days, and 94 to 107 cm when grown in Bogota with 14 long days prior to start of short days.

B. Foliage:
*Color (upper surface).*—147A.
*Color (under surface).*—147B.
*Shape.*—See photograph.

CHART A

| CULTIVAR | CANTATA | VOLARE |
|---|---|---|
| Ray floret color | Light pink | Light purple |
| Capitulum form and type | Flat daisy | Flat daisy |
| Diameter across face of capitulum | 76 to 89 mm | 80 to 83 mm |
| Flowering response | | |
| in Salinas | 48 to 52 days | 49 to 52 days |
| in Bogota | 59 to 63 days | 63 to 70 days |
| Peduncle length: | | |
| 1st lateral Salinas | 10 to 15 cm | 13 to 15 cm |
| 4th lateral Salinas | 15 to 25 cm | 18 cm |
| 1st lateral Bogota | 13 to 20 cm | 13 to 18 cm |
| 4th lateral Bogota | 18 to 23 cm | 18 to 23 cm |
| Low night temperature tolerance | Excellent | Excellent |

COMPARISONS MADE OF PLANTS GROWN AS SINGLE STEM SPRAY CUT MUMS IN SALINAS, CALIFORNIA AND IN BOGOTA, COLOMBIA

I claim:

1. A new and distinct Chrysanthemum plant named Cantata, as described and illustrated.

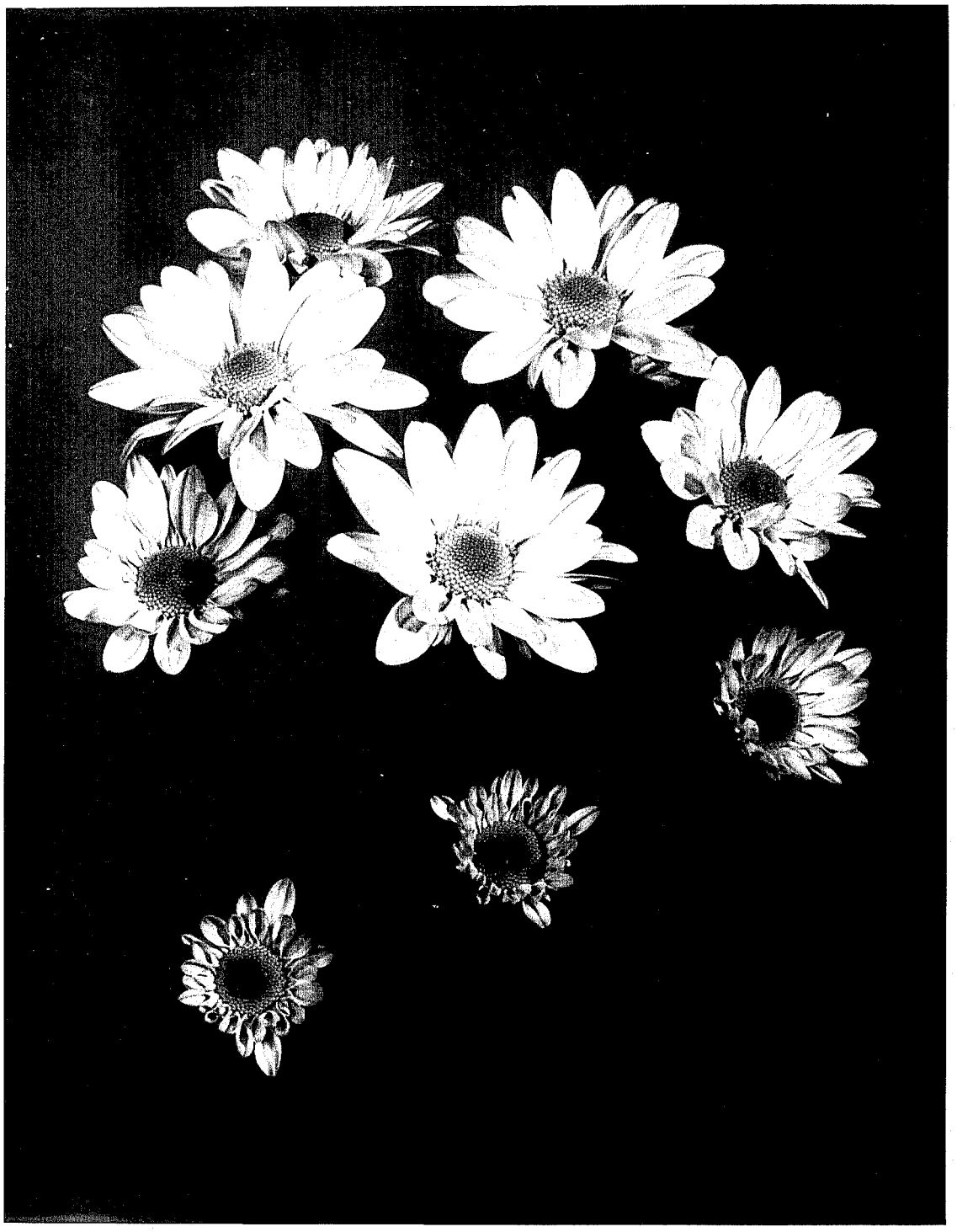

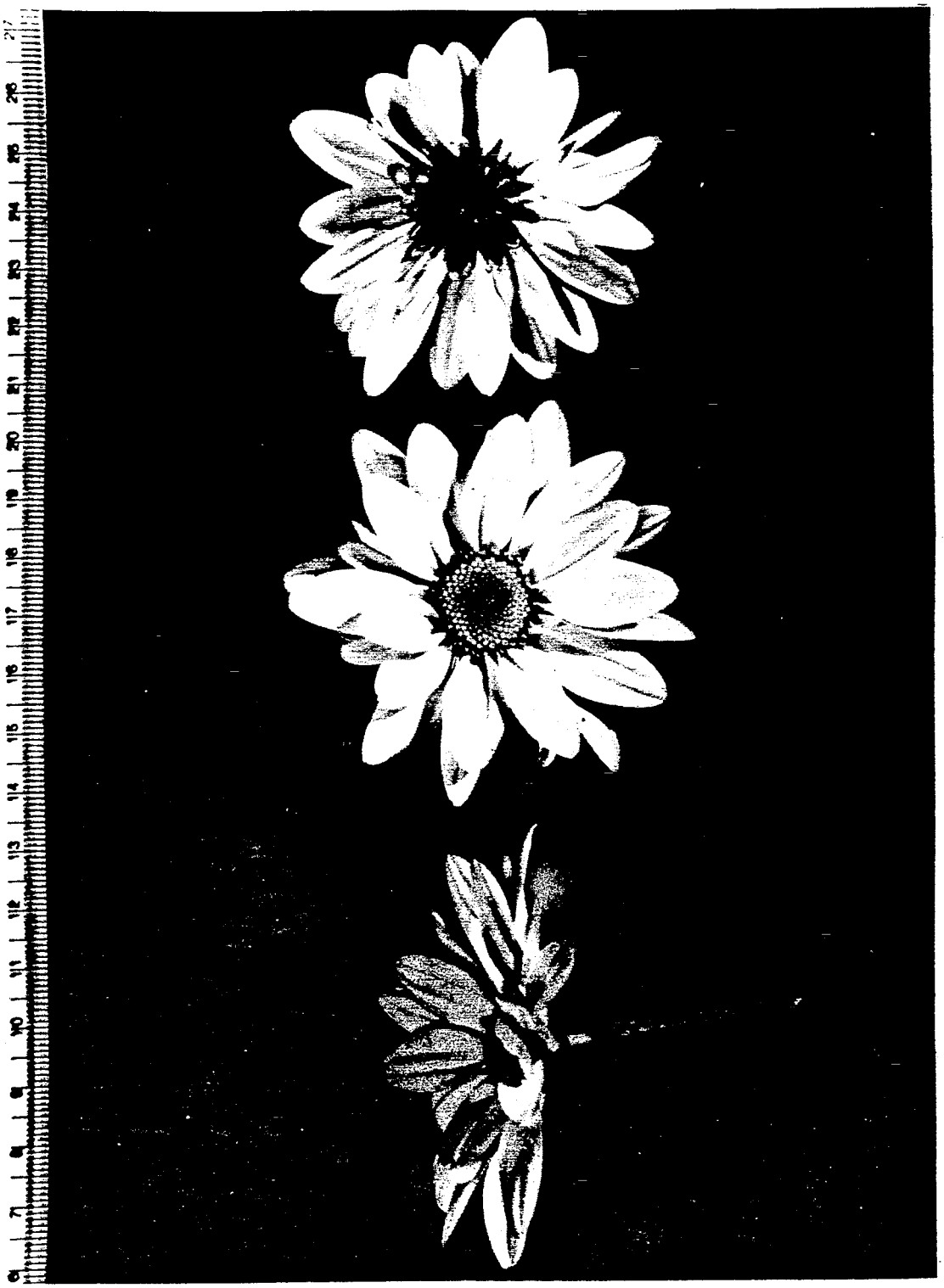

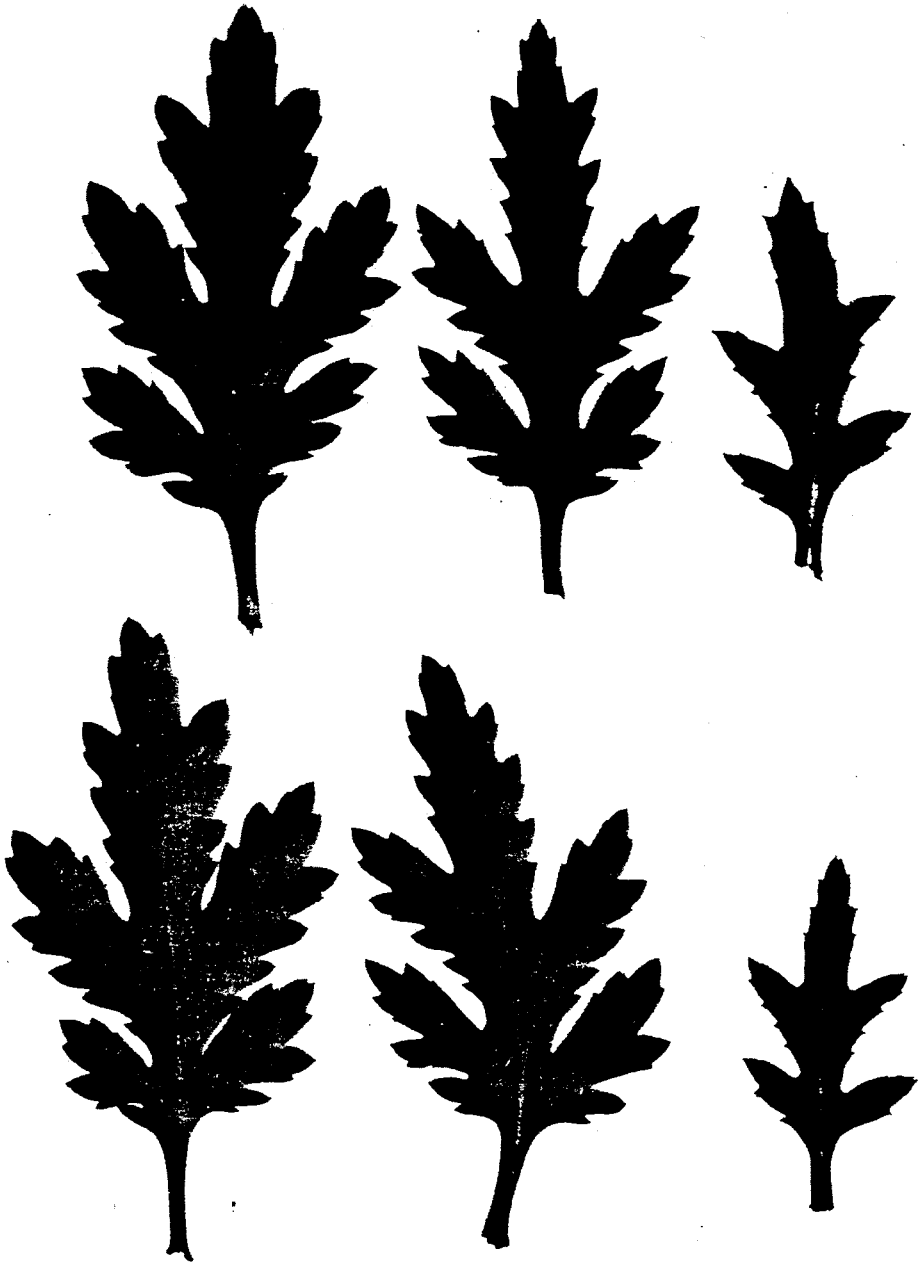

* * * * *